United States Patent [19]

Reich et al.

[11] Patent Number: 5,563,233
[45] Date of Patent: Oct. 8, 1996

[54] POLYETHER POLYURETHANE POLYMERS AND GELS HAVING IMPROVED ABSORPTION AND SLIP PROPERTIES

[75] Inventors: Murray H. Reich, Princeton; Ken Nelson, Lambertville; Jirina Kuzma, Princeton, all of N.J.

[73] Assignee: Tyndale Plains-Hunter, Ltd., Ringoes, N.J.

[21] Appl. No.: 340,606

[22] Filed: Nov. 16, 1994

[51] Int. Cl.$^6$ ................................................. C08L 75/08
[52] U.S. Cl. ................................................. 528/76
[58] Field of Search ........................................ 528/76

[56] References Cited

U.S. PATENT DOCUMENTS

| | | | |
|---|---|---|---|
| 3,822,238 | 7/1974 | Blair et al. | 528/59 |
| 4,235,988 | 11/1980 | Fildes et al. | 514/772.1 |
| 4,496,535 | 1/1985 | Gould et al. | 424/402 |
| 4,810,582 | 3/1989 | Gould et al. | 428/423.1 |
| 4,830,860 | 5/1989 | Ranade | 424/486 |
| 5,000,955 | 3/1991 | Gould et al. | 424/497 |
| 5,120,816 | 6/1992 | Gould et al. | 528/76 |
| 5,273,742 | 12/1993 | Gould et al. | 424/78.08 |
| 5,334,691 | 8/1994 | Gould et al. | 528/76 |

*Primary Examiner*—Thomas Hamilton, III
*Attorney, Agent, or Firm*—Mathews, Woodbridge & Collins

[57] ABSTRACT

An improved polyurethane is prepared by reacting a diol component and an organic diisocyanate with critical selection of the amount of water in the reaction mixture and the diol component. The diol component is a long chain polyoxyethylene glycol optionally mixed with a low molecular weight polyoxyethylene glycol. A tough gel can be formed by mixing the polyurethane in a diol or triol and water solution. The tough gel can be used in burn and wound dressings, electroconductive pads, high slip materials and surgical implants. An optically clear gel can also be formed. Solutions and emulsions can be formed of the polymer and can be combined with fillers to form face creams and antiperspirants. A film can cover one side of the gel for burn and wound applications. The gel can be used in squeeze tubes and in spray cans in burn wound care dressings and industrial applications and in bags and containers for use in plastic surgery implants.

11 Claims, No Drawings

POLYETHER POLYURETHANE POLYMERS AND GELS HAVING IMPROVED ABSORPTION AND SLIP PROPERTIES

BACKGROUND OF THE INVENTION

1. Field of the Invention

The present invention relates to novel polyether polyurethanes which form tough gels, soft elastic gels, high slip materials and solutions specifically adapted for use in burn and wound care dressings, plastic surgery implants, heat and cold-retentive applications, pressure absorbing applications, electroconductive surgical pads, drug delivery systems, antiperspirants, tubing and molded devices, medical, cosmetic and industrial applications.

2. Description of the Related Art

U.S. Pat. No. 4,810,582 of a common ownership to the present invention describes blends of hydrophilic polyurethanes derived from blending a polyoxyalkylene glycol with a polyester polyurethane. The polyester polyurethane is the reaction product of an aromatic diisocyanate and a polyol. The polymer blend absorbs water when immersed in water and retains its mechanical strength. A film formed from the polymer blend can be used in a burn dressing. The film can contain a medicament, hormone or a steroid. The polymer blend can be extruded and molded. For example, the polymer blend can be used in a diaphragm, cannula, contact lens, corneal prosthesis and dialysis membrane.

U.S. Pat No. 5,000,955 of common ownership with the present invention relates to thermally reversible polyurethane hydrogels. This patent describes that when polyether polyurethanes are formed under anhydrous conditions they form hydrogels in water. The hydrogels are solids at room temperature but liquefy at higher temperatures, such as body temperature. The hydrogels can be used for, controlled delivery and sustained release of an active agent. The active agent is encapsulated in the gel matrix for immobilizing and protecting the agent. On lowering the viscosity of the hydrogel by raising the temperature, the active material becomes mobile. The active material can include drugs, cosmetic additives, salts, and food additives. The hydrogels can also be used as nontoxic culture media for the growth of microorganisms. In addition, the polymer forms a solution at 25% solids in ethanol having a viscosity of 1200 cps which can be used for the preparation of face masks and dry-skin protectants.

U.S. Pat. Nos. 3,822,238 ('238 patent) and 3,975,350 ('350 patent) describe a class of hydrophilic polyurethane polymers which absorb water with the concomitant formation of a stable, water-insoluble hydrogel. The '350 patent describes that when the cross-linked polymers are in the wet state they range from gel-like polymers to polymers being compliant, soft and flexible. Alternatively, about 0.01 to about 0.6% of a polypropylene polyol, preferably 0.05 to 0.5%, more preferably from 0.06 to 0.4%, with a molecular weight of about 100 to about 7000 can be added. The hydrogels can be used in various applications such as in coatings, linings, membranes, absorbent, swellable fabrics, gauzes and the like. The hydrogels can be cured to form solid or shaped bodies, such as rod sheets and tubes. However, the '238 and the '350 patents have the shortcomings of not being soluble in dilute glycol/water solutions, not forming jelly-like gels at moderate concentrations, of retaining their shape in water, and not becoming flowable at high temperatures, making them capable of being extruded into forms and not having sufficient mechanical strength to be tough at body temperature which property is preferable for certain applications. The '350 patent teaches a polymer that precipitates out of a methanol solution upon the addition of water and the polymer is cross-linked.

U.S. Pat. No. 5,273,742, of common ownership to the present invention describes a method for replacing ocular fluid in an eye and for replacing intra-articular fluid in a joint by introducing an aqueous solution of a water soluble hydrogel in an amount of 0.5% to 7% weight of polymer. In both applications, the polymer forms an injectable solution of the water-soluble hydrogel. However, the water-soluble hydrogel does not form a tough gel at body temperatures.

U.S. Pat. No. 5,120,816 of common ownership to the present invention describes a polyurethane resin having improved tear strength in which the amount of water in the reaction mixture is claimed to be in the range of about 1.0% to about 2.5% weight percent. The use of a large amount of water provides insoluble polymers which have high strength in water. However, this type of polyurethane resin does not form tough gels.

SUMMARY OF THE INVENTION

It has now been found that by carefully selecting and controlling the amount of an alkylene glycol and polyoxyalkylene diol component and controlling the amount of water in the reaction mixture, the polyurethane can be modified to produce gels with properties ranging from soft and elastic to firm, resilient and tough gels. Optionally, an amine equivalent can be used for at least a portion of the water in the reaction mixture. A tough gel can be formed by mixing an amount of the polymer in a triol or diol and water solution. The properties of the tough gel of the present invention are surprising in view of the prior art directed to hydrophilic polyurethanes.

According to one aspect of the invention, a tough gel is formed by the steps of mixing a gel forming polyurethane polymer in a diol or triol and water solution. The reaction product comprises a mixture of a diol component comprising a polyoxyalkylene glycol selected from polyoxyethylene glycol having a number average molecular weight of from about 400 to about 20,000, polyoxypropylene glycol having a number average molecular weight of number average molecular weight of about 200 to about 4,000, polyether polycarbonate having a number average molecular weight of about 400 to about 3,000, a low molecular weight alkylene glycol selected from ethylene glycol, propylene glycol, 2-ethyl-1,3-hexanediol, tripropylene glycol, triethylene glycol, 2,-4-pentanediol, 2-methyl-1,3-propanediol, cyclohexanediol, cyclohexanedimethanol, 2-methyl-1,3-pentanediol dipropylene glycol and diethylene glycol, and mixtures thereof having a number average molecular weight of about 1,000 to about 9,000, an organic diisocyanate and a water equivalent in an amount comprising from about 0.001% to about 0.8% of the reaction mixture in an equivalent mole weight ratio of NCO/OH of from about 0.3 to about 1.2. Alternatively, the alkylene glycol can be omitted from the reaction mixture. An amount of a triol selected from glycerol and trimethylolethane can used be in an amount of about 0.01% to about 5.0% of the reaction mixture. Preferably, the diol is polyoxyethylene.

The amount by weight of the polymer in the tough gel is preferably in the range of about 0.05% to about 50%. The tough gel is particularly useful for burn and wound applications, post-surgery dressings, plastic surgery and surgical implants, electroconductive pads, drug delivery systems, high slip materials, cold and heat retentive applications, pressure absorbing applications, cosmetic applications, hand cleaning gels and force dampening materials for reducing the impact of falls.

Alternatively, an amount of an amine, such as diglycolamine, can be used for at least a portion of the water equivalent used in the reaction mixture. The amount of water in the reaction is reduced by substituting an amine for the portion of water used for forming the tough gel. The amount of water can be reduced by adding an amount of an amine consisting of 50-400% of the amount of water used in the reaction mixture. Urea groups are derived from the amine. Preferably, about 0.01% to about 0.2% of water and about 0.03% to about 10.0% of diglycolamine is used in the reaction mixture.

In other aspects of the present invention, the polymer can be modified by adding an amount of a low molecular weight polyoxyethylene having a number average molecular weight of about 400 to about 2,000 in combination with a polyoxyethylene having a molecular weight of about 6,000 to about 14,000. The water in the reaction mixture of this polymer is preferably about 0.01% to 0.8%. The polymer can be used to form an optically clear tough gel. The optically clear gel is preferably useful in burn and wound dressings, squeeze tubes for burn and wound dressings, cosmetic and industrial applications, plastic surgery implants and electroconductive pads and high slip materials. Optionally, the media for the gel may be water alone. Polymers containing specific diols can be used to thicken polar media such as polyglycol/water, glycol/water mixtures to produce highly viscous gels.

Other aspects of the invention involve forming solutions and emulsions of the above described polymers. Fillers, oils, colorants and fragrants can be added to the solutions for cosmetic, industrial and medical applications such as mascara, body and face creams and antiperspirants, shaving cream and de-icing coatings. The solutions and emulsions can be injected into the body to replace body fluids.

DETAILED DESCRIPTION OF THE INVENTION

The present invention is based on the discovery that a class of polyether polyurethanes more fully described herein formed from the reaction product of a diol component, diisocyanate and water are advantageous in burn and wound dressings, plastic surgery implants and electroconductive surgical pads. Alternatively, an amount of amine, such as diglycolamine can be used for at least a portion of the water equivalent to form the reaction product. A gel formed of the polyether polyurethane has improved toughness properties at room and body temperatures. In burn and wound applications a tough gel is used which is defined as having the physical properties of being a tough, firm and resilient, and does not flow at body temperature. The viscosity of the tough gel is greater than that which can be measured with conventional viscosity measurements, such as with a Brookfield Viscometer. The tough gel of the present invention preferably has sufficient strength to impede a 30 gram weight at room temperature. In other applications, such as antiperspirants, the gel is formed to be tough and capable of flowing at body temperatures. In still other applications, the gel is formed to be a soft, elastic, tough formless jelly.

A first aspect of the present invention pertains to a hydrophilic polyurethane comprising the reaction product of a diol component comprising a polyoxyalkylene glycol selected from polyoxyethylene glycol having a number average molecular weight of from about 400 to about 20,000, polyoxypropylene glycol having a number average molecular weight of about 200 to about 4,000 and polyoxytetramethylene glycol having a number average molecular weight of about 200 to about 4,000, and polyether polycarbonate having an average molecular number weight of about 400 to about 3,000, about 0.01% to about 10% of a low molecular weight alkylene glycol selected from ethylene glycol, propylene glycol, 2-ethyl-i, 3-hexanediol, tripropylene glycol, triethylene glycol, 2, -4-pentanediol, 2-methyl-i, 3-propanediol, cyclohexanediol, cyclohexanedimethanol, 2-methyl-1,3-pentanediol, dipropylene glycol, diethylene glycol, and mixtures thereof having a number average molecular weight of about 1,000 to about 9,000, an organic diisocyanate and water in an amount comprising from about 0.001% to about 0.8% of the reaction mixture, wherein the amount by weight of the polyoxyalkylene in the reaction mixture is about 20% to about 96% in a mole weight ratio of NCO/OH of from about 0.3 to about 1.2. Preferably, the preferred polyoxyalkylene is polyoxyethylene. It has been found that the alkylene glycol affects a hard segment of the polyurethane and the polyoxyalkylene glycol affects hydrophilicity of a soft segment of the polyurethane.

Alternatively, an amine can be used in the reaction for at least a portion of the water equivalent. Preferably, about 0.01% to about 0.2% water and about 0.03% to about 10.0% of the amine water equivalent is used in the reaction mixture. Preferably, in a reaction for producing burn and wound care dressing about 0.015% to about 0.07% water and about 0.15% to about 2.0% amine is used in the reaction for producing burn and wound dressings. Most preferably about 0.02% to about 0.07% water and about 0.1% to about 0.6% of amine to the reaction components is used in the reaction.

Amines which can be used in the reaction are ethylene diamine, propylene diamine, monoethanolamine, diglycolamine, propylene diamine, Jeffamine D1-230, D-400, D-2000, D-4000, ED0600, ED-900, ED-2001. The hydroxylamines and the Jeffamines are manufactured by Texaco Chemical Company. Preferably, the amine used in the reaction is hydroxylamine, more preferably, the amine is monoethanolamine and digylcolamine, and most preferably the amine is diglycolamine.

A small amount of triol can also be used in the reaction. The amount of triol used in the reaction is in the range of about 0.001% to about 5.0% of the reaction components with about 0.010% to about 0.8% of water, and preferably the amount of water is about 0.005% to about 0.3%. Preferably, the amount of triol is about 0.02% to about 0.5% and most preferably the amount of triol is about 0.03% to about 0.2% of the reaction components. The triol can be selected from glycerol, trimethylolethane, polyols such as soribtan, glucose and sorbitol, LG-650, AR11-34, E-452, AR11-27, LHT-240, LG-56, LG-168, LHT-112 and LHT-42. The above triols are available from ARCO. The triols can also be selected from tetrols manufactured by BASF under the tradename of Tetronic and Tetronic R surfactants, 304, 504, 50R1, 50R4 and 70R4. The addition of a triol in the reaction introduces branching in the reaction product and aids in swelling of the polymer.

The polyoxyethylene glycols are available from Union Carbide Corporation under the trademark and designation Carbowax, such as Carbowax® 8000 and Carbowax® 1450 wherein the numbers represent the number average molecular weight.

The polyoxypropylene glycols are available from various sources such as from the PPG series of ARCO NIAX® PPG 1025, PPG425, PPG-725, PPG 1225 and PPG 2025 wherein the numbers represent the number average molecular weight. Triols are also available from ARCO as Niax polyols 11-34, LG-650, LG-56, LG-168, LHT-28, LHT-240.

The polyoxytetramethylene glycols are available from E.I. DuPont de Nemours as Terathanes 600, 1000, 1400, 2000, 2900.

Polyetherpolycarbonate is available from BASF under the tradename polytetrahydrofuran 1000 CD and 2000 CD.

A block polyoxyalkylene polymer can also be used in the reaction. For example, a propylene oxide terminated block of ethylene glycol manufactured by BASF under the tradename Pluronic R and a ethylene oxide terminated block of propylene glycol manufactured by BASF under the tradename of Pluronic can be used for the polyoxyalkylene in the reaction.

Preferably, the amount of the polyoxyalkylene diol used in the reaction is at least about 20% to about 96% of the total reaction components. More preferably, the polyoxyalkylene diol is used in an amount of at least about 50% of the total reaction components. Most preferably, the polyoxyalkylene diol is used in an amount of at least about 55% by weight of the total reaction components.

The alkylene glycols can be purchased at chemical supply houses. For example, propylene glycol can be purchased from Aldrich Chemical Company as 1,2 propane diol.

An especially preferred isocyanate for forming the reaction product is methylene bis(cyclohexyl-4 -isocyanate). In addition to methylene bis(cyclohexyl-4-4'-isocyanate) other diisocyanates can be used in preparing suitable hydrophilic polyurethane polymers. These other diisocyanates include both aliphatic and aromatic types although the aliphatics are preferred. Representative examples of the preferred aliphatic diisocyanates include, but are not limited to tetramethylene diisocyanate, hexamethylene diisocyanate, trimethylene diisocyanate, trimethylhexamethylene diisocyanate, cyclohexyl 1,2 diisocyanate, cyclohexylene 1,4 diisocyanate, and aromatic diisocyanates such as 2,4-toluene diisocyanates and 2,6-toluene diisocyanates. Also suitable are the isocyanate equivalents which form urethane linkages as exemplified by nitrile carbonates, such as adiponitrile carbonate of the formula (see U.S. Pat. No, 4,810,543, of common ownership herewith).

The polymers are prepared by reacting the polyoxyalkylene diols with diisocyanates. The equivalent weight ratio of NCO/OH is about 0.30 to about 1.20, more preferably from about 0.60 to about 0.98, and most preferably from about 0.65 to about 0.97. The OH in the NCO/OH ratio includes hydroxyl groups from the diols, triols, glycol and ethanol amines, amines and water having a reactivity of at least two. The equivalent NCO/OH ratio for producing burn and wound care dressings is about 0.84 to about 0.96.

The amount of water in the reaction mixture comprises about 0.001% to about 0.8%, preferably from about 0.3% to about 0.8%, more preferably from about 0.015% to about 0.7%, still more preferably from about 0.02% to about 0.4% and most preferably from about 0.02% to about 0.3%, based upon the weight of the total reaction components.

The water equivalent in the reaction typically reacts with an isocyanate group to form carbamic acid and afterwards converts into an amine which reacts with another isocyanate group to form a urea group. At high temperatures and excess isocyanate urea can react with another isocyanate group to form biuret groups. The amine equivalent reacts directly with the isocyanate to form the urea groups which can result in a more controlled reaction.

In making the polyurethane of the invention, the glycol components are formed into a homogeneous mixture which is then reacted with diisocyanate, the reaction is catalyzed with known catalysts such as tertiary amine, tin salts and organic tin esters, such as dibutyl tin dilaurate and stannous octoate. Preferably the catalysts used in the reactions are stannous octoate and dibutyl tin dilaurate, manufactured by Air Products and Chemicals as $T_9$ and $T_{12}$.

The diols are subjected to vacuum at 0° to 120° C. to obtain a water content of about 0.001% to 2%, preferably about 0.002% to about 1%, more preferably about 0.003% to about 0.5% and most preferably about 0.01% to about 0.1%. The mixture is analyzed for water by a standard water determination method such as Karl Fisher and infrared, and a water determination instrument made by Arizona Instrument Company. After the water analysis, the remainder of the water or amine specified in the formulation is added. The diisocyanate is added to the mixture and the mixture heated to an initiation temperature from about 50°–90° C. The catalyst is added and the mixture is stirred, poured into a container and heated at about 20° C. to about 140° C. for about one minute to several hours and days.

In an alternative method, a semi-batch reaction is used in which the diols are heated and vacuum dried; the mixture is analyzed for water; and a predetermined amount of additional water or amine is added. The catalyst is added to the mixture. Diisocyanate is added to another reactor and heated under dry nitrogen. Two streams of heated reactive mixtures are mixed in a predetermined ratio in a tube and allowed to flow into a pan, extruder, static and dynamic mixers, trough, conveyor belt, or other container. The mixture is allowed to react further at a temperature from about 20° to 140° C., preferably from about 30° to about 135° C., more preferably from about 40° to about 130° C., and most preferably from about 60° to about 120° C. for about one minute to about one week, preferably for about 5 minutes to about 240 minutes, more preferably from about 10 minutes to about 120 minutes. The reaction can be completed at room temperature.

It has surprisingly been found that controlling the amount of water or a water equivalent, or amine equivalent substituted for a portion of the water equivalent, such as a 50%–400% equivalent, to small amounts in the reaction mixture provides properties of the polymer for effective use in burn and wound dressings. It has been found experimentally, for example, that a polymer with a small but sufficient amount of urea groups for forming a tough jelly-like gel can be obtained by controlling the amount of the water equivalent and the amount of amine equivalent. The polymers formed with the controlled amount of water and amine in the reaction mixture provide gels with improved water absorbency, toughness and high viscosity at body temperatures. These polymers have increased absorption properties and are advantageous for burn and wound dressings.

A 3% concentration of the above-described polymer in 60/40 propylene glycol to water solution has a viscosity in the range of about 1 cps to about 2,000,000 cps. For other applications, polymers with low levels of urea groups can produce soft, flexible gels at low levels of polymer in the gels. It is desirable to use low levels of polymers in heat and cold retentive products to keep the costs low.

For burn and wound care dressings applications, the diol is selected to have a number average molecular weight which can be used to form a predetermined polymer with a viscosity at a 3% polymer concentration in 60/40 propylene glycol/water solution of from about 1 cps to about 300,000 cps, preferably from about 2 cps to about 100,000 cps, more preferably from about 3 cps to about 50,000 cps, still more preferably from about 5 cps to about 8,000 cps and most preferably from about 10 cps to about 500 cps. The polymer has a viscosity at a 2% polymer concentration in a 20/80 propylene glycol to water solution of about 1 cps to about 2,000,000 cps, preferably about 2 cps to about 1,000,000 cps, more preferably about 4 cps to about 500,000 cps, still more preferably from about 6 cps to about 100,000 cps and most preferably from about 10 cps to about 1,000 cps.

The properties of the polyurethane are especially suitable for forming tough gels, plastic surgery implants, coatings and gels which can be contained and distributed from squeeze tubes.

The polymers are also useful in the manufacture of dialysis membranes, oxygen exchange membranes, invertebral discs, and absorbent packaging inserts. The polymers can also be used as blood oxygenators, intrauterine devices, oral delivery systems, battery separator membranes, adhesives, eye bandages, gas permeable membranes, gas filters, protective coatings for automotive and electronic parts, cosmetic applications, paint additives for water-soluble paints, used to coat insecticides, herbicides and fertilizer to control the leaching rate and antigrafitti coatings. Preferably, the polymers are used in plastic surgery implants, heat and cold retentive products such as heat and cold packs, post-surgery bandages and dressings, electroconductive surgical pads, burn and wound dressings, delivery of drugs to the skin, and shock absorbers for arthritic joints.

The polymers can also be used in high slip durable materials, tubing and materials. Preferably, for high slip durable materials, the amount of polyoxyethylene diol used in the reaction is at least about 30% of the reaction components, the water content is less than about 0.5% of the reaction components and the NCO/OH ratio is at least about 0.70. More preferably, the polyoxyethylene diol used in the reaction for high slip polymers is at least about 40%, the water content is less than about 0.4% of the reaction components and the NCO/OH ratio is at least about 0.75. Still more preferably, the polyoxyethylene in the reaction for high slip polymers is at least about 50%, the water content is in the range of about 0.005% to about 0.3% and the NCO/OH ratio is at least about 0.80. Most preferably, the polyoxyethylene used in the reaction for high slip polymers is at least 75%, the water content is less than about 0.25% and the NCO/OH ratio is at least about 0.87. Alternatively, about 0.01% to about 3.0% of ethylhexyl diol can be added to the reaction in which the water content is in the range of about 0.01% to about 0.20% of the reaction components. Also, about 0.01% to about 0.8% of a diglycolamine can be substituted for a portion of the water content in which the water content is in the range of about 0.005% to about 0.4% of the reaction components. Alternatively, about 0.001% to about 5.0% of a triol can be used in the reaction and preferably about 0.01% to about 3.0% of a triol is used in the reaction. The triol can be selected from trimethylolethane glycerol, LG-650, tetrols and AR11-34. The high slip polymers can be used as coatings and to make extruded, molded and dip coated products with high slip properties.

In a second aspect of the invention the polyether polyurethanes described above are formed into a tough gel of improved strength, heat stability, heat and cold retentivity and integrity. The tough gel is formed by the steps of mixing a gel forming polyurethane in a diol or triol and water solution. In other applications, a gel is formed which is soft and elastic or has good adhesive properties. The different properties of the gel are obtained by varying the amount of polymer in the gel and/or the concentration of glycol in the diol and triol and water solution.

The polyurethane comprises the reaction product of a mixture of a diol component comprising a polyoxyalkylene glycol selected from polyoxyethylene glycol having a number average molecular weight of from about 400 to about 20,000, polyoxypropylene glycol having a number average molecular weight of about 200 to about 4,000 and polyoxytetramethylene glycol having a number average molecular weight of about 200 to about 4,000, polyether polycarbonate having a number average molecular weight about 400 to about 3,000, a low molecular weight alkylene glycol selected from ethylene glycol, propylene glycol, dipropylene glycol, diethylene glycol, 2-ethyl-1,3-hexanediol, tripropylene glycol, triethylene glycol, 2,-4-pentanediol, 2-methyl-1,3propanediol, cyclohexanediol, cyclohexanedimethanol, 2-methyl-i, 3- pentanediol and mixtures thereof, an organic diisocyanate and water in an amount comprising from about 0.001% to about 0.8% of the reaction mixture in a equivalent weight ratio of NCO/OH of from about 0.3 to about 1.2. The polyoxyalkylene is preferably polyoxyethylene diol. Preferably, the amount of alkylene glycol is about 0.01% to about 10.0%, more preferably about 0.01% to about 6.0%, most preferably about 0.05% to about 5.0%. Alternatively, the polymer can be modified by eliminating the alkylene glycol as a reaction component Preferably the amount of water used in the polymer reaction product for forming the polyether polyurethane of the tough gel is from about 0.001% to about 0.7%, more preferably from about 0.01% to about 0.4%, and most preferably from about 0.03% to about 0.2%. An amine equivalent of about 0.15% to about 1.0% can be substituted for the water used in the reaction. Preferably, the equivalent weight ratio of NCO/OH used in the reaction product of the tough gel is from about 0.4 to about 1.2, more preferably from about 0.55 to about 0.99, still more preferably from about 0.75 to about 0.98 and most preferably from about 0.80 to about 0.95.

Preferably, in the tough gel forming reaction product, an amount of at least 40% of the polyoxyethylene diol can be used in the reaction, more preferably at least 60% and most preferably at least 80% of polyoxyethylene of the total weight of the reactants is used. In addition, the tough gel forming reaction product which forms a tough gel useful for burn and wound care dressing applications preferably has an amount of water added in the reaction mixture of from about 0.02% to about 0.18%.

The concentration of the diol or triol in the water solvent solution is preferably at least about 1%. Preferably, the concentration of the diol or triol in the water solution is at least about 3% and more preferably the concentration of the diol or triol is at least about 5% of the solution and most preferably the diol or triol is at least 8% of the solution. The mixture is heated with stirring until the mixture is homogeneous. Thereafter, the mixture is cooled. The heating and cooling steps can be repeated until a tough gel is formed.

Alternatively, water alone can be used as the solvent with the polyurethane tough gel. The water solvent can be advantageous for applications such as breast implants and plastic surgery implants.

The amount by weight of the polymer used in forming the tough gel is in the range of about 0.05% to about 50%, more preferably about 2% to about 35% and most preferably about 3% to about 30%.

For burn and wound care dressings, drug delivery systems, heat and cold retentive applications, pressure absorbing products and electroconductive surgical pads, the amount of polymer in the tough gel is about 1.0% to about 50.0%, preferably from about 5.0% to about 40.0%, more preferably from about 8.0% to about 30.0%, still more preferably from about 12% to about 28%, and most preferably from about 14.0% to about 25.0%. For drug delivery systems, the amount of polymer in the tough gel can be about 5.0% to about 30.0%, preferably from about 7.0% to about 25.0% and most preferably from about 8.0% to about 22.0%. For plastic surgery implants, heat and cold retentive and pressure absorbing products, the amount of polymer in the tough gel can be from about 0.1% to about 50.0%, preferably from about 0.25% to about 45%, more preferably from about 0.5% to about 40.0%, and most preferably from about 1.0% to about 30.0%.

Diols that can be used in the diol and water solution for forming the tough gels can be selected from the group of propylene glycol, ethylene glycol, diethylene glycol, triethylene glycol, tripropylene glycol, 2-methyl-1,3-pentanediol, pentanediol, dipropylene glycol, polyoxypropylene glycol having a number average molecular weight of about 400, butanediol and ethylhexyl diol. Triols that can be used in triol and water solutions forming the tough gels are glycerol, trimethylolethane, LP-650 and AR11-34 manufactured by ARCO Corporation. Preferably, the diol or triol solutions used in a gel for an industrial application are ethylhexyl diol, propylene glycol, ethylene glycol, neopentyl glycol, glycerol, and dipropylene glycol. The diol and triol preferable for use in a gel for a medical application such as burn and wound dressings, cold and heat retentive and pressure absorbing products, and plastic surgery and surgical implants are propylene glycol and glycerol.

A tough gel is formed which is useful in burn and wound dressings by mixing the reaction product in a glycerol and water solution. The glycerol solution can comprise a solution having about 0.05% to about 70% of glycerol to the total mixture components. More preferably, concentrations of about 2% to about 50% and most preferably a concentration of about 10% to about 40% of glycerol to the total mixture components is used. A mixture of the reaction product in a propylene glycol/water solution forms a gel preferable for burn and wound dressings. Preferably, the propylene glycol is added in a concentration of about 2% to about 35% and most preferably a concentration of about 5% to about 20% of the total mixture components.

The viscosity of the tough gels impedes a 30.0 gram stainless steel ball from moving through the gel. The viscosity of the tough gels for use in burn and wound care dressings and electroconductive surgical pads are such that a 30-gram stainless-steel ball will move through about 150 grams of gel in an 8-ounce jar at no more than about 5.0 mm/min, preferably about 3.0 mm/min, more preferably no more than about 2.0 mm/min, and most preferably no more than about 1.0 mm/min. At about a body temperature of 37° C. or room temperature the rate will be no more than about 50.0 mm/min, preferably about 40.0 mm/min, more preferably no more than about 30.0 mm/min, still more preferably no more than about 25.0 mm/min and most preferably no more than about 20.0 mm/min. The viscosity of tough gels for use in heat and cold applications has a rate of no more than about 20.0 mm/min, preferably about 15.0 mm/min, more preferably about 10.0 mm/min, and most preferably about 5.0 mm/min. The viscosity of soft elastic gels has a rate of no more than about 15.0 mm/min and preferably 10.0 mm/min at room temperature.

The tough gels used in burn and wound care dressings can have an absorbency of at least about 0.30 gram of water per gram of gel, preferably, about 0.75 gram of water per gram of gel, more preferably about 1.0 gram of water per gram of gel, still more preferably at least about 1.5 grams of water per gram of gel, and most preferably about at least about 1.75 gram of water per gram of gel.

Improved physical properties of the tough gel of the present invention include water absorbtivity, integrity, flexibility, improved mechanical strength, high electroconductivity, heat and cold retentivity, gas permeability, improved moisture vapor transmission rate, clarity, and adhesion to glass, metal, foil, woven cloth, non-woven cloth, bone and skin. The tough gel provides high viscosity at low and body temperatures.

The above described tough gels' characteristics translate into superior burn and wound dressings made from the gels. The gels can be poured into hydrophobic films, bags, and squeeze tubes for use as dressings, heat and cold applications, coatings, post-surgical dressings and implants.

Electroconductive surgical pads require moderate adhesion to the skin so that the pad can be readily removed and sufficient adhesion to obtain good contact with the skin and prevent burns. The gel should be compatible with the polyurethane adhesive used to coat the metal foil and be electroconductive. The gel of the present invention has the characteristics of integrity, strength, toughness, electroconductivity and adhesive properties which properties provide improved electroconductive surgical pads.

The tough gels are biocompatible and are beneficial in plastic surgery implants including breast and nose implants. The tough gels are useful in contraceptive devices, heat and cold retentive applications, coatings, de-icing coatings, anti-fogging agents, protective heels, hair styling gels, drug delivery systems, water-absorbents, carrier systems for active agents, and ostomy sealing devices.

The gels can include additives such as, for example, antibiotics, hydrocolloids, medical compounds, electrolytes, cell growth materials, nutrients, inorganic and organic fillers selected from the group of sodium and calcium carbonate, silicates, alginates, carbon black, and metal oxides such as: titanium dioxide; silica; and zinc oxide, emulsifiers such as glycerol trioleate, oils such as lanolin, drugs, cells, enzymes and cancer-fighting compounds.

A third aspect of the present invention relates to a hydrophilic polyurethane comprising the reaction product of a diol comprising a high molecular weight polyoxyalkylene glycol selected from polyoxyethylene glycol having a number average molecular weight of from about 400 to about 20,000, polyoxypropylene glycol having a number average molecular weight of about 200 to about 4,000, polyoxytetramethylene glycol having a number average molecular weight of about 200 to about 4,000, polyether polycarbonate having a number average molecular weight about 400 to about 3,000, optionally mixed with a low molecular weight polyoxyethylene diol having a number average molecular weight of about 400 to about 2,000, an alkylene glycol, an organic diisocyanate, water in an amount of about 0.005% to about 0.8% for the high molecular weight polyoxyalkylene or water in an amount of about 0.001% to about 0.7% for the mixture of the high molecular weight and low molecular weight polyoxyethylene glycol in an equivalent mole weight ratio of NCO/OH of from about 0.5 to about 1.2. Preferably, at least 30% of polyoxyethylene glycol of about 8000 average number molecular weight, more preferably at least 35%, most preferably at least 40% of polyoxyethylene diol of the total reaction mixture is used.

Alternatively, an amine equivalent can be used for an amount of water in the reaction mixture. An amount of about 0.15% to about 6.0% of amine, based on diglycolamine, is used with 0.001% to about 0.25% of the water, more preferably of about 0.02% to about 0.20% of the water, and most preferably of about 0.025% to about 0.10% of the water.

The alkylene glycol in the reaction mixture preferably includes about 0.01% to about 5% of the total reaction mixture of a hydrophobic glycol selected from the group of 2-ethyl-1,3-hexanediol 2,-4-pentanediol, 2-methyl-1,3-propanediol, cyclohexanediol, and cyclohexanedimethanol, still more preferably 2-ethyl-1,3-hexanediol and cyclohexanedimethanol, and most preferably 2-ethyl-1,3-hexanediol are used in the reaction mixture. The amount of the hydrophobic glycol is preferably from about 0.01% to about 5%, still more preferably from about 0.02% to about 3%, and most preferably from about 0.05% to about 2.5% of the total reaction mixture.

Additionally, small amounts of triol can be used in the reaction with about 0.01% to about 0.8%, preferably with about 0.01% to about 0.25% water. Preferably, the amount of triol, can be about 0,001% to about 1.0%, preferably from about 0.01% to about 0.5%, and most preferably from about 0.02% to about 0.3%. The triol is selected from glycerol, trimethylolethane, LG-650, tetrols and AR11-34.

The high molecular weight polyoxyethylene glycol preferably has a number average molecular weight of about 4,000 to about 12,000. The low molecular weight polyoxyethylene glycol preferably has an average number molecular weight of about 400 to about 2,000 and most preferably an average molecular weight of 1450. Preferably, the amount of low molecular weight polyoxyethylene in the mixture of the high molecular weight polyoxyethylene and the low molecular weight polyoxyethylene is about 1% to about 60%, more preferably about 3% to about 40% and most preferably about 4% to about 35% of the total reaction mixture. Preferably, the NCO/OH ratio of the polymer is about 0.6 to about 1.0 and more preferably from about 0.65 to about 0.99 and still more preferably from about 0.70 to about 0.98.

Preferably, about 0.01% to about 0.4% of water is added to a reaction mixture having the high molecular weight glycol and about 0.01% to about 0.35% of water is added to a reaction mixture having the high molecular weight and low molecular weight glycol. Preferably, the amount of diglycolamine is from about 0.01% to about 10%, more preferably from about 0.1% to about 6% of the total reaction mixture. Alternatively, about 1% to about 40% of a polyetherpolycarbonate diol of a 600 to 3000 molecular weight is added with at least about 35% polyoxyethylene diol, at a NCO/OH ratio of about 0.60 to about 0.98, with about 0.01% to about 0.4% water or amine equivalent of the total reaction product.

The gels' properties can be varied by decreasing the amount of polymer in the gel and increasing the amount of diol in the diol and water solution. An elastic soft gel can be formed with about 1.0% to about 15% of the polymer in a glycol to water solution in the range of about 10/90 to about 95/5. Preferably, the elastic soft gel is formed with about 3.0% of the polymer and in a 20/80 glycol to water solution. A pliable soft gel with excellent adhesive properties can be formed with about 1.0% to about 10% of polymer in a 40/60 glycol/water solution. It has been found that a soft gel with excellent payoff and spread properties can be formed with about 5.0% of polymer comprising a polyether polycarbonate diol in a 20/80 glycol/water solution. A tough gel can be formed at 5% of polymer in a 20/80 glycol/water solution.

A 3% concentration of the above-described polymer in 60/40 propylene glycol to water solution has a viscosity in the range of about 1 cps to about 500,000 cps for a soft and elastic gel.

The above-described polymer in 40/60 propylene glycol/water the polymer swells to form a soft, elastic, uniform homogeneous clear gel. The polymer forms these uniform gels in glycol/water solutions at concentrations of less than about 15% of polymer, preferably less than about 10%, and most preferably less than about 6%. This polymer can be used as a binder and toughener in antiperspirants and as moisturizers and to form durable high slip coatings, tubing and materials for use in medical, cosmetic, and industrial applications. This polymer can also be used to form optically clear solutions and gels for use in antiperspirants, deodorants, cosmetic applications, cleaning gels, burn and wound dressings, plastic surgery implants, delivery of drugs, electroconductive surgical pads, cold and heat retentive applications, pressure absorbing products and skin creams containing drugs and health care compounds. For example, a pressure absorbing product can be used in a cushion or a mattress.

Alternatively, about 0.01% to about 4% of hydrophobic diol selected from ethylhexyl diol, pentanediol and 2-methyl-1,3propanediol, preferably ethylhexyl diol, can be added to the reaction. The water used in the reaction is from about 0.01% to about 0.3% and preferably from about 0.02% to about 0.2%. Also, alternatively, about 0.001% to 5% of a triol can be added, preferably about 0.01% to about 3%. The triol is selected from the group of trimethylolethane, glycerol, LG-650, and AR11-34. Diglycolamine can be used in the reaction in an amount of about 0.01% to about 0.8%. The water content in the reaction is in the range of about 0.005% to about 0.4% of the reaction components.

For use in high slip durable products, the amount of polyoxyethylene diol of a 8000 molecular weight is preferably greater than about 40%, the amount of polyoxyethylene diol of low molecular weight of a number average 1000 to 3000 in the reaction mixture is preferably about 10% to about 30% of the reaction components. The water content is less than about 0.4% of the reaction components. Preferably, the water content is in the range of about 0.01% to about 0.3% and most preferably the water content is in the range of about 0.02% to about 0.2%. The NCO/OH ratio is at least about 0.70. A hydrophobic diol from about 0.01% to about 4.0% selected from ethylhexyldiol and pentanediol, preferably pentanediol, can be used in the reaction. The high slip polymers can be used as coatings and to make extruded, molded, and dip coated products.

A preferable gel for use in burn and wound applications has a NCO/OH ratio of about 0.84 to about 0.96. Water in the reaction is used in an amount of about 0.02% to about 0.15%. The gel can also include about 0.01% to about 0.8% of a triol. The triol can be glycerol, trimethylolethane, LG-650, tetrols and AR11-34. Further, the gel can include about 0.01% to about 4.0% of a hydrophobic diol. The diol can be ethylhexyl diol, pentanediol and 2-methyl-1,3-propanediol.

In a fourth aspect of the present invention, an optically clear gel is formed by mixing a gel forming polyurethane in a diol or triol and water solution. The gel forming polyurethane comprises hydrophilic polyurethane comprising the reaction product of a diol comprising a high molecular weight polyoxyethylene glycol having an average molecular weight of from about 4,000 to about 15,000 optionally mixed with a low molecular weight polyoxyethylene diol having a number average molecular weight of about 400 to about 2,000, an alkylene glycol, an organic diisocyanate, water in an amount of about 0,005% to about 0.7% for the high molecular weight polyoxyethylene or water in an amount of about 0,001% to about 0.6% for the mixture of the high molecular weight and low molecular weight polyoxyethylene glycol in a equivalent weight ratio of NCO/OH of from about 0.6 to about 1.0. Alternatively, an amine such as a diglycol amine, in the range of about 0.03% to about 8.0% can be used for at least a portion of the water equivalent. Optionally, a triol can be used in the reaction with about 0.01% to about 0.8% of water, preferably with about 0.01% to about 0.25% water. Preferably, the amount of triol can be about 0.001% to about 1.0%, preferably from about 0.01% to about 0.5%, and most preferably from about 0.02% to about 0.3%. The triol is selected from glycerol, trimethylolethane, LG-650 and AR11-34.

The viscosity of the clear gels impedes a 30 gram stainless steel ball moving through the gel. At 2.0% concentration of polymer in glycol/water mixtures, the viscosity can vary at room temperature from about 5 cps to about 2,000,000 cps, depending upon the desired application, with a different range being preferred for different applications. Viscosity can vary at about 2% polymer concentration in 20/80 propylene glycol/water solution from about 9 cps to about 2,000,000 cps. For polymers made with about 4.0% to about 18.0% of about 1000 to 2000 average number molecular weight polyoxyethylene glycol, the viscosity can vary from about 9 cps to about 1,000,000 cps, and for about 22.0% to about 28.0% of about 1000 to about 2000 average number molecular weight polyoxyethylene glycol, the viscosity may vary from about 10 cps to about 1,000,000 cps.

The amount by weight of the polymer used in forming the optically clear tough gel is in the range of about 0.01% to about 50.0%. Preferably the amount of polymer in the gel is about 3.0% to about 12.0% for applications of dispensing the gel from squeeze tubes and electroconductive surgical pads. The amount of polymer in the gel is preferably about 14.0% to about 25.0% for burn and wound dressings. The amount of polymer for plastic surgery implants is preferably about 0.5% to about 15.0%, more preferably from about 0.8% to about 12.0%, most preferably from about 0.9% to about 10.0%, still more preferably from about 1.0% to about 5.0%.

The amount of polymer in the propylene glycol/water solution for use in cosmetic applications is about 0.1% to about 15.0%, preferably from about 0.2% to about 10.0%. The amount of polymer in the propylene glycol/water solution for use in heat and cold-retentive and pressure absorbing products is preferably from about 1.0% to about 25.0%, preferably from about 2.0% to about 20.0%, and more preferably from about 2.5% to about 15.0%. The above described diol and triol and water solutions can be used in forming the optically clear gel.

The above described clear gels characteristics translate into superior burn and wound dressings made from the gels. The burn or wound can be observed through the gel during the healing process. The optically clear gels can be poured into hydrophobic films, bags, and squeeze tubes for use as dressings, coatings, cold and heat-retentive applications and implants. The electroconductive property of optically clear tough gels provides improved electroconductive surgical pads.

In a fifth aspect of the present invention, an article of manufacture is formed from the above-described tough gels and optically clear gels and a film covering at least one side of the gel.

The film can be of polyethylene, polypropylene, Polyoxytetramethylene, copolymers of ethylene, copolymers of propylene, polyurethane, and hydrophilic polyurethane films. A hydrophilic film made according to U.S. Pat. No 4,789,720 hereby incorporated by reference into this application can be used in the article of manufacture. Preferably the hydrophilic polyether polyurethane film has a moisture vapor transmission rate (MVTR) of at least 500 grams/meter$^2$/24 hours. More preferably, the hydrophilic polyether polyurethane film has a MVTR of at least 1000, more preferably about 1500, and most preferably the film has an MVTR of at least 2000 grams/meter$^2$ /24 hours. It will be understood that for certain applications, 1500 MVTR will be most preferred, and for other applications, a 2000 MVTR film would be most preferred, and that for still other applications, 1000 MVTR film will be most preferred.

The hydrophilic polyether polyurethane film can be formed from at least 40% of a polyoxyethylene diol having a number average molecular weight of about 800 to about 8,000 and at least 2% of a polyoxypropylene diol having a number average molecular weight of about 1,000 to about 3,000. Preferably the polyoxyethylene diol has a number average molecular weight 1,000 to 6,000. Preferably at least 3% of polyoxypropylene diol, more preferably 4%, and most preferably at least 5% of polyoxypropylene diol is used in forming the film. The polyurethane film can also comprise polyoxytetramethylene diols having a number average molecular weight of about 500 to about 3000. Preferably, less than 60% of polyoxytetramethylene diol, more preferably less than about 45%, and most preferably less than about 35% is used in the reaction mixture for forming the film.

A burn and wound care dressing made from the tough gels covered by a film absorbs significant amounts of exudate and is slightly acidic. The burn and wound dressing has high oxygen permeability and high moisture vapor transmission, thereby enhancing its absorptive and healing properties. A gel covered with the high moisture vapor transmission rate (MVTR) film of the present invention has improved water absorption properties with a water transmission rate (WTR) at 35° C. of 15,000 grams/meter$^2$ /24 hours. In comparison, a conventional dressing covered with hydrophobic film has a WTR of 700 grams/meter$^2$/24 (For example, a conventional dressing as manufactured by NDN as Clear Site.

An alternative article of manufacture of the present invention, can be formed by fully enclosing the tough gel in the hydrophilic film. This article of manufacture can be used in plastic surgery implants.

A sixth aspect of the present invention relates to solutions and emulsions formed from the above-described hydrophilic polyurethane polymers. In the sixth aspect of the invention, the polyether polyurethanes described above are formed into a highly viscous uniform mixture of improved integrity and heat and cold retentivity for use in plastic surgery implants. The highly viscous material is formed by the steps of mixing a high viscosity polyurethane in a diol or triol and water solution. The polyurethane can be formed of the reaction product of a diol component comprising a high molecular weight polyoxyalkylene glycol selected from polyoxyethylene glycol having a number average molecular weight of about 400 to about 20,000, polyoxypropylene glycol and polyoxytetramethylene glycol having a number average molecular weight of about 200 to about 4,000 optionally mixed with a low molecular weight alkylene glycol selected from ethylene glycol, propylene glycol, dipropylene glycol, tripropylene glycol, triethylene glycol in a diethylene glycol and polyoxyethylene diol having a number average molecular weight of about 1000 to about 1600, an organic diisocyanate, water in an amount comprising from about 0,001% to about 0.8% of the reaction mixture, preferably about 0.35% of the reaction mixture and an NCO/OH ratio of about 0.5 to about 1.0, preferably about 0.6 to about 0.98.

The amount of diol in the reaction mixture is about 20% to about 90%. Preferably, the high molecular weight polyoxyalkylene glycol is polyoxyethylene glycol having a molecular weight of about 800 to about 15,000.

Optionally, a triol can be used in the reaction with about 0.01% to about 0.8% of water, preferably with about 0.01% to about 0.25% water. Preferably, the amount of triol can be about 0.001% to about 1.0%, more preferably from about 0.01% to about 0.5%, and most preferably from about 0.2% to about 0.3%. The triol used can be selected from glycerol, trimethylolethane, LG-650 and AR11-34.

Solutions of the polymer have a concentration of about 0.2% to about 12% of the polymer, more preferably about 0.3% to about 8% of the polymer. For plastic surgery implants, the viscosity is at least about 2000 cps, preferably at least about 4000 cps, most preferably at least about 6000 cps. It will be appreciated that the concentration of polymer capable of forming a solution will vary depending on the number average molecular weight of the polymer. The solvent used to form the solution can be water or a diol or triol and water solution.

An emulsion can be formed by adding an emulsifying agent such as glycol trioleate or ethylhexyl diol to the solution. For emulsions, the diol or triol can comprise about 0.1% to about 80%, preferably about 0.5% to about 50%, more preferably about 1% to about 40% and most preferably from about 2% to about 30% of the solvent. Polymer level in the emulsion can comprise about 0.01% to about 40%, preferably about 0.1% to about 20%, more preferably from about 0.2% to about 10%.

The solution is formed by mixing granules of the polymer in the solvent. The solution can be mixed in a roller mill. Preferably, the solution is mixed for at least an hour on the roller mill. The solution is heated at a temperature between 50° C. to about 90° C. for at least one hour until the solution is homogeneous. Preferably, the viscosity of the solution is in the range of about 10 cps to about 10,000 cps.

The solutions of polymer have the characteristics of a natural body fluid being non-toxic, non-inflammatory and viscoelastic. The solutions have the improved properties of high strength, clarity, breathability, absorbtivity and toughness.

The solutions of the polymers herein described can be combined with oils, colorants, fragrants, propellants, cosmetic additives and fillers. The fillers can include zinc and titanium oxide, carbonates, and silicates for use in medical and cosmetic applications such as in protective skin gels and creams, therapeutic creams with drugs, cosmetic and shaving creams, mascara, antiperspirants, body creams, make-up base, and cosmetic coatings. The emulsifiers can be used to form materials for industrial applications such as protective coatings for electronic parts, de-icing coatings, and anti-fogging coatings.

The polymer solutions can be injected into the eye as intraocular and extraocular devices, joints. The polymer solutions can be injected into the intervertebral discs, blood vessels and the body cavities. The polymer solutions can assist in the correction of rheumatologic problems such as damage, lameness, inflammation and swelling and the like. The polymer solution can be removed upon elimination of the body condition.

The following examples are provided to illustrate the nature of the present invention and are not to be construed as limiting the scope thereof, which scope is specifically defined in the appended claims.

EXAMPLE 1

A polyether polyurethane was prepared by mixing 402 parts of Carbowax® 8000 polyoxyethylene glycol (Union Carbide Corporation) and 11.2 parts of diethylene glycol with stirring and heating at 65° C. to 70° C. The heated mixture forms a homogeneous melt which is vacuum dried to 0.030% water, as measured by Karl Fisher method, and 0.022 parts water are added to bring the total water content to 0.15 parts. While continuing to stir, 42 parts of methylene bis(cyclohexyl-4-isocyanate) of Desmoder W® diisocyanate, Mobay Chemical Corporation was added, during which the temperature decreased. The NCO/OH ratio of the diisocyanate was 0.96. When the temperature reached 65° C., 0.37 ml of $T_{12}$ catalyst (dibutyl tin dilaurate, Air Products and Chemicals, Inc.) was added. The reaction mass was poured into a polypropylene pan, and the pan was placed in a circulating oven at 100° C. for one hour.

EXAMPLE 2

The polymer made in Example 1 was cooled to ambient room temperature. The polymer mass was cut into small pieces which were mixed with a solution of a ratio of 60/40 propylene glycol to water to form a mixture containing 3.0% solids to obtain a viscosity of 315 cps.

The polymer mass was mixed with a solution of a ratio of 20/80 propylene glycol to water to form a mixture containing 2% solids to obtain a viscosity of 53,000 cps.

The polymer mass was mixed with a solution of a ratio 20/80 of propylene glycol to water to form a mixture containing 10% solids. This mixture formed a tough gel.

EXAMPLE 3

15.0 grams of the polymer mass of Example 1 was mixed on a roller mill with 75.0 grams of a solution of a ratio of 20/80 propylene glycol to water. After rolling overnight, the mixture was heated in an oven at 50-60° C. for one hour. The rolling and heating processes were repeated several times until a uniform gel was obtained.

A wound dressing was formed of the gel by heating and pouring the heated gel into a wound dressing form. The gel was covered with a hydrophobic film. The wound dressing can be used for wound and burn care.

The gel was heated and poured into a plastic bag for use in heat-retentive and pressure absorbing products, implants for delivery of drugs and plastic surgery implants.

An electroconductive surgical pad was formed by heating the gel and pouring the heated gel into a form having an adhesive-coated metal foil.

EXAMPLE 4

A polyether polyurethane was prepared by mixing 402 parts of Carbowax® 8000 polyoxyethylene glycol (Union Carbide Corporation) and 11.2 parts of diethylene glycol with stirring and heating at 65° C. to 70° C. The heated mixture forms a homogeneous melt which is vacuum dried to 0.019% water, as measured by Karl Fisher method, additional water was added to bring the total water content to 0.08 parts. While continuing to stir, 41.6 parts of methylene bis(cyclohexyl-4-isocyanate) of Desmoder W® diisocyanate was added. The NCO/OH ratio of the diisocyanate was 0.96. When the temperature reached 64° C., 0.38 ml of $T_{12}$ catalyst was added. The reaction mass was poured into a polypropylene pan, and the pan was placed in a circulating oven at 100° C. for one hour.

The polymer mass was dissolved in a solution of a ratio of 60/40 propylene glycol to water to form a mixture of 3% solids to obtain a viscosity of 7100 cps.

The polymer mass was dissolved in a solution or a ratio of 60/40 propylene glycol to water to form a mixture of 10% solids. The mixture formed a tough gel.

10.0 grams of the polymer mass was mixed on a roller mill with 90.0 grams of a solution of a ratio of 20/80 propylene glycol to water. After rolling overnight, the mixture was heated in an oven at 50°–65° C. for one hour. The rolling and heating processes were repeated several times until a uniform gel was obtained.

The gel was heated and poured into a flat mold and placed in water. The gel increased in weight from 23.05 grams to 56.88 grams over a period of ten days resulting in 1.47 grams of water per gram of gel.

A wound dressing was formed by the gel heating and pouring the heated gel into a wound dressing form. The gel was covered with a hydrophobic film. The wound dressing can be used for wound and burn care.

The gel was heated and poured into a plastic bag for use heat-retentive and pressure absorbing products, such as ice packs, dressings and implants for delivery of drugs and plastic surgery implants.

EXAMPLE 5

A polyether polyurethane was proposed by mixing 402 part os Carbowax® 8000 polyoxyethylene glycol and 11.2 parts of diethylene glycol with stirring and heating at 65° C. to 70° C. The heated mixture forms a homogeneous melt which is vacuum dried to 0,030% water and 0.066 parts water are added to bring the total water content to 0.21 parts. While continuing to stir, 42 parts of methylene bis(cyclohexyl-4-isocyanate) of Desmoder W® diisocyanate was added. The NCO/OH ratio of the diisocyanate was 0.94. When the temperature reached 55° C. , 0.37 ml of $T_{12}$ catalyst was added and the mass exothermed to 65° C. The reaction mass was poured into a polypropylene pan, and the pan was placed in a circulating oven at 100° C. for one hour.

The polymer mass was dissolved in a solution of a ratio of 60/40 propylene glycol to water to form a mixture containing 3% solids to obtain a viscosity of 122 cps.

The polymer mass was dissolved in a solution of a ratio of 20/80 propylene glycol to water to form a mixture containing 2% solids to obtain a viscosity of 1380 cps.

The polymer was dissolved in a ratio of 20/80 propylene glycol to water to form a mixture of containing 10% solids. The mixture formed a tough gel. The polymer can be dissolved at 15% solids in a 10/90 propylene glycol/water solution, heated to about 80° C., and cooled to about 45° C., a drug can be added, and cooled to room temperature. The gel can be used to deliver a drug through the skin. The gel was heated and poured into a squeeze tube made by Tubed Products.

The tough gel can be used in wound dressings and implants.

EXAMPLE 6

A polyether polyurethane was proposed by mixing 402 part of Carbowax® 8000 polyoxyethylene glycol and 11.2 parts of diethylene glycol with stirring and heating at 65° C to 70° C. The heated mixture forms a homogeneous melt which is vacuum dried to 018% water, and 0.39 parts water are added to bring the total water content to 0.46 parts. While continuing to stir, 42 parts of methylene bis(cyclohexyl-4-isocyanate) of Desmoder W® was added. The NCO/OH ratio of the diisocyanate was 0.86. When the temperature reached 68° C. 0 37 ml of $T_{12}$ catalyst was added. The reaction mass was poured into a polypropylene pan, and the pan was placed in a circulating oven at 100° C. for one hour.

The polymer mass was dissolved in a solution of a ratio of 60/40 propylene glycol to water to form mixture containing 3% solids to obtain a viscosity of 90 cps.

The polymer mass was dissolved in a solution of a ratio of 20/80 propylene glycol to water to form a mixture containing 2% solids to obtain a viscosity of 670 cps. The polymer was dissolved in water to form a mixture containing 2% solids to obtain a viscosity of 4900 cps.

The polymer mass was dissolved in a solution of a ratio of 20/80 propylene glycol to water to form a mixture of 10% solids. The polymer can be dissolved at 15% solids in a 10/90 propylene glycol/water solution, heated to about 80° C., and cooled to about 45° C., a drug can be added, and cooled to room temperature. The gel can be used to deliver a drug through the skin. The mixture formed a tough gel. The tough gel can be used for dressings and implants.

EXAMPLE 7

A polyether polyurethane was prepared by mixing 269 parts of Carbowax® 8000 polyoxyethylene glycol 114 parts of 1450 polyoxyethylene glycol (Union Carbide Corporation), and 12 parts diethylene glycol with stirring and heating at 65° C. to 70° C.

The heated mixture forms a homogeneous melt which is vacuum dried to 0.044% water, as measured by the Karl Fisher method and 0.079 parts water are added to bring the total water content to 0.92 parts.

While continuing to stir, 55 parts of methylene bis (cyclohexyl-4-isocyanate) was added during which time the temperature decreased. The NCO/OH ratio was 0.92. When the temperature reached 63° C., 1.0 ml dibutyl tin dilaurate was added and the mass exothermed to 80° C. The mass was heated at 100° C. for one hour.

The polymer mass was dissolved in a solution of a ratio of 60/40 propylene glycol to water to form a solution of 3% solids to obtain a viscosity of 26 cps. The solution was optically clear.

The polymer was dissolved in a solution of a ratio of 20/80 propylene glycol to water to form a mixture containing 2% solids with a viscosity of 11 cps. This mixture can be used in cosmetic applications.

The polymer mass was dissolved in a solution of 90/10 propylene glycol to water to form a mixture containing 9% solids. The mixture formed a tough gel. The gel was heated and poured into a squeeze tube made by Tubed Products. The gel can be squeezed out of the tube for wound care dressings.

The polymer mass was dissolved in a solution of 20/80 propylene glycol water to form a mixture containing 10% solids. The mixture formed a tough gel. The gel can be used in wound care dressings and plastic surgery implants. The polymer was insoluble in water.

EXAMPLE 8

A polyether polyurethane was prepared by mixing 257 parts of polyoxytetramethylene diol having an average molecular weight of 1000, 210 parts of polyoxytetramethylene diol having an average molecular weight of 2000, 37 parts of polyoxypropylene diol having an average molecular weight of 625, 28 parts of polyoxypropylene diol having an average molecular weight of 2025, 378 parts of polyoxyethylene diol having an average molecular weight of 1450, 379 parts of polyoxyethylene diol having an average molecular weight of 4500, and 124 parts of ethylene glycol with stirring and heating. To the mixture was added 7 parts of water. While continuing to stir, 805 parts of methylene bis(cyclohexyl- 4-isocyanate) were added during which period the temperature decreased. The NCO/OH ratio was 0.95. When the temperature reached 65° C., 3.4 ml of stannous octoate added, and the mass exothermed. The mass was heated in an oven at 100° C. for about one hour.

The polymer was extruded at about 280°–330° F. in a Killion extruder to obtain a film having a thickness of one mil film. The film had an (moisture vapor transmission rate) MVTR of 3,230 and water transmission rate (WTR) of 27,410 g/meter$^2$/24 hours. The film had a tensile strength of 3210 lb/sq in, an elongation of 680%, and a tear strength of 250 lb/in.

EXAMPLE 9

The gel made in Example 4 was heated, poured into a wound dressing mold and covered with a film and the composite can be used as wound care and burn dressing. A simulated dressing was tested in the standard MVTR cup used to measure water transmission rate (WTR), except that the cup was inverted as a means of measuring water transmission when the material is in contact with water. Under these conditions the simulated dressing had a WTR of 16,900 grams per meter$^2$ /day at a temperature of 35° C. Under the same conditions, Gel-Syte, manufactured by Baxter Healthcare, a commercial wound care dressing had a WTR of 780 per meter$^2$ /day at 35° C. and Clearsite manufactured by NDM had an MVTR of 700 per meter$^2$ /day 35° C.

EXAMPLE 10

A mixture of 443 parts of polyoxypropylene diol having an average molecular weight of 1025, 327 parts of polyoxypropylene diol having an average molecular weight of 2025, 546 parts of polyoxyethylene diol having an average molecular weight of 1450, 546 parts of polyoxyethylene diol having an average molecular weight of 4500, and 170 parts of ethylene glycol was stirred and heated. To the mixture was added 13 parts of water. While continuing to stir 1149 parts of methylene bis(cyclohexyl-4-isocyanate) were added. The NCO/OH ratio was 0.95. When the temperature reached about 65° C., 3.4 ml of stannous octoate added. The mass was heated in an oven at 100° C. for one hour.

The polymer was dissolved at 10% solids in ethanol and ethyl acetate, and the solution was cast to provide a film. At one mil thickness, the film had an MVTR of 4,040 and an WTR of 28,060 g/meter-square/24 hours, a tensile strength of 5,240 pounds per square inch, and an elongation of 600%. The film was used to cover gels of Examples 4 and 19 for use in burn and would dressings. The film can be used to enclose gels of the present invention for use in plastic surgery implants.

EXAMPLE 11

A mixture of 592 parts of carbowax 8000 polyoxyethylene diol, 183 parts of polyoxyethylene glycol having an average molecular weight of 1450, and 23 parts of diethylene glycol was stirred and heated. The mixture was vacuum dried to 0.046% water, as measured by the Karl Fisher method, and 0.08 parts water was added to bring the total water in the reaction mixture to 0.45 parts. While stirring the mixture, 107 parts of methylene bis (cyclohexyl-4-isocyanate) were added. The NCO/OH ratio was 0.92. When the temperature reached about 63° C., 0.75 ml of stannous octoate was added. The mass was heated in an oven at 100° C. for about one hour.

The polymer was dissolved at 3% solids in solution ratio of 60/40 in a propylene glycol/water to provide a clear solution having a viscosity of 62 cps. The polymer was dissolved at 2% solids in solution of a ratio of 20/80 propylene glycol/water to obtain a viscosity of 116 cps and in water at 2% solids to obtain a viscosity of 300 cps.

The polymer was dissolved at 10% solids in 20/80 propylene glycol/water to form a tough clear gel for wound care dressings and implants. A gel was formed comprising 9% of the polymer in a solution of a ratio of 10/90 propylene glycol/water. The gel was heated and can be poured into a squeeze tube made by Tubed Products. The gel can be readily squeezed out of the tube for use in wound care dressings and industrial applications.

EXAMPLE 12

A mixture of 644 parts of 8000 polyoxyethylene diol, 139 parts of 1450 polyoxyethylene diol and 22 parts of diethylene glycol was stirred and heated. The mixture was vacuum dried to 0.053% water, as measured by the Karl Fisher method, bringing the total water in the reaction mixture to 0.43 parts. While stirring the mixture of diols and water, 102 parts of methylene bis(cyclohexyl-4-isocyanate) were added during which period the temperatures decreased. The NCO/OH ratio was 0.94. When the temperature reached 65° C., 0.75 ml of stannous octoate was added. The mass was heated in an oven at 100° C. for about one hour.

The polymer was dissolved at 3% solids in a ratio of 20/80 propylene glycol/water to provide a solution having a viscosity of 48,000 cps. The polymer was dissolved in water at 2% solids to provide a solution having a viscosity of 240,000 cps. A tough optically clear gel was formed by dissolving the polymer at 10% solids in a solution having a ratio of 20/80 propylene glycol to water. A gel was formed comprising 9% polymer in a solution of 10/90 water/propylene glycol which can be used for burn and wound care dressings and implants. The polymer can be dissolved at 15% solids in a 10/90 propylene glycol/water solution, heated to about 80° C., and cooled to about 45° C., a drug can be added, and cooled to room temperature. The gel can be used to deliver a drug through the skin. The gel was heated and poured into a squeeze tube made by Tubed Products.

A gel was formed of 10% of the polymer in a solution of 20/80 propylene glycol/water and was poured into an electroconductive surgical form. The gel was removed from the form. The gel had good adhesion to skin and good flexibility.

EXAMPLE 13

A mixture of 322 parts of 8000 polyoxyethylene diol, 70 parts of 1450 polyoxyethylene glycol, and 11 parts of diethylene glycol was stirred and heated. The mixture was vacuum dried to a water content of 0.052%, as measured by the Karl Fisher method, the total water content was 0.21 parts. While stirring the mixture, 47 parts of methylene bis(cyclohexyl-4-isocyanate) was added. The NCO/OH ratio was 0.87. When the temperature reached about 65° C., 0.6 ml of stannous octoate was added. The mass was heated at 100° C. for about one hour.

The polymer was dissolved at 3% solids in a solution of 60/40 propylene glycol/water to form a clear solution having a viscosity of 33 cps and at 2% solids in a solution of 20/80 propylene glycol/water to obtain a viscosity of 19 cps, and at 2% in water to obtain a viscosity of 17 cps. A mixture of 15% of the polymer in a solution of 20/80 propylene glycol/water was heated to about 70° C., was mixed at room temperature to form a tough gel for use in wound care dressings. The heated gel was poured over hydrophilic adhesive-coated metal foil for use as an electroconductive surgical pad. The gel in the electroconductive pad had desirable adhesion conductivity, optical clarity. The polymer can be dissolved at 15% solids in a 10/90 propylene glycol/ water solution, heated to about 80° C., and cooled to about 45° C., a drug can be added, and cooled to room temperature. The gel can be used to deliver a drug through the skin.

Gels made with 15% and 17% gel from the polymer can also be used in burn and wound dressings, breast implants, and in a squeeze tube.

EXAMPLE 14

A mixture of 402 parts of 8000 polyoxyethylene diol and 11 parts of diethylene glycol was agitated and heated. The mixture was vacuum dried to 0.024 % water and 0.38 part water was added to bring the total water in the reaction mixture to 1.4 parts. While stirring the mixture, 43 parts of methylene bis(cyclohexyl-4-isocyanate) were added, during which the temperature deceased. The NCO/OH ratio was 0.64. When the temperature reached 62° C., 0.38 ml of dibutyl tin dilaurate was added. The mass was heated at 100° C. for about one hour.

The polymer was dissolved at 3% solids in a solution of 60/40 propylene glycol/water to provide a viscosity of 38 cps and at 2% solids in a solution of 20/80 propylene glycol/water to provide a viscosity of 15 cps. The polymer was mixed with water at 5% solids and heated at 60° C. to form a gel.

To 100 grams of the gel were added 10 grams of pola wax, 5 grams of phospholipid SV, 1 gram of lanolin oil, 4 grams of avocado oil, 2 grams of crodamoll PHP, 0.5 grams of crodaroy calendola, and 10 grams of seamollient which consists of water and algae extract, and 1 gram of germaben II. The mixture formed a homogeneous cream which was easily spread on the skin, was non-irritating to the skin, had a moist feeling on the skin and did not contain lumps. The cream was used as a face and hand cream.

EXAMPLE 15

A mixture of 14030 parts of 8000 polyoxyethylene diol and 392 parts of diethylene glycol was agitated and heated in a reactor. The mixture was vacuum dried at about 180° F. to 0.055% water and 5.9 parts water were added to bring the total in the reaction mixture to 13.7 parts. A separate reactor contained 1455 parts of methylene bis(cyclohexyl-4-isocyanate). To the diols was added 23.8 cc of dibutyl tin dilaurate. Then the solids and catalyst were heated at 175° to 185° F., and the isocyanate was heated to 110°–115° F. and both liquids were forced out at under nitrogen pressure using a piston cylinder at about a ratio of 0.102. Twelve shots of liquid were pumped into a polypropylene tub and heated for one hour at 100° C. The NCO/OH ratio was 0.88.

The polymer was dissolved at 3% solids in a solution of 60/40 propylene glycol/water to provide a viscosity of 77 cps and at 2% solids in a solution of 20/80 propylene glycol/water to provide a viscosity of 179 cps. The polymer was mixed with a solution of 20/80 propylene glycol/water at polymer concentrations of 17% and 19% and heated to about 80° C. to form gels and poured into wound care forms. The gels had absorbencies of greater than 2.5 grams per gram of gel. The gels can be used for burn and wound care dressings and plastic surgery implants. The gels were tough at room and at body temperature.

The polymer was mixed at 2% concentration with a solution of 20/80 ethylhexyl diol/water and heated at 80° C. to form an emulsion at room temperature.

To respective mixtures of 2% polymer in a solution of 20/80 propylene glycol/water was added 2% oxide, 5% zinc oxide, 2% and 5% titanium dioxide, 2% glycerol trioleate. Zinc oxide dispersed readily into the mixture, and formed a light paste. The zinc oxide mixture can be used as a first aid cream and a sunscreen cream. The mixture had a smooth feeling. The mixtures with titanium dioxide were milky and made a good paste. The titanium dioxide dispersed evenly in the mixture. The titanium dioxide mixtures spread well and left a white paint-like coating.

A uniform emulsion was formed with glycerol trioleate. A mixture of 2% polymer in a solution of 20/80 propylene glycol/water was slightly cloudy, and became optically clear and basic with 2% sodium carbonate. The emulsion had a viscosity of 10,000 cps. The emulsion can be used for cosmetic and industrial applications.

The polymer was mixed at 10% solids with a solution of a ratio of 20/80 mixtures of described alcohols, diols, and triols to water. The polymers were roller milled for about one hour at room temperature, placed for about 1.5 hours in an oven at 80° C. to 90° C., and then placed on the roller mill again. The polymer formed homogeneous solutions with ethanol and isopropyl alcohol having respective viscosities of 40,000 cps and 14,600 cps. The polymer formed homogeneous gels with solutions of ethylene glycol, triethylene diol, dipropylene glycol, diethylene glycol, and tripropylene diol. The polymer formed a tough gel with glycerol. The viscosity of the above gels was too high to measure with a Brookfield viscometer. The polymer formed tough gels at 10% solids in solutions of 30/70 glycerol/water, 40/60 glycerol/water and 50/50 glycerol/water. The gels can be used in burn and wound care applications, plastic surgery implants, electroconductive surgical pads, and drug delivery systems.

Solutions of polymer at 0.5% to 4% solids in diol/water and triol/water were prepared. The solutions can be used in the above-described medical, cosmetic, and industrial applications.

EXAMPLE 16

A mixture of 644 parts of 8000 polyoxyethylene diol, 139 parts of 1450 polyoxyethylene glycol and 22 parts of diethylene glycol was stirred and heated. The mixture was vacuum dried to a water content of 0.062%, as measured by the Karl Fisher method, and 0.079 part water was added to bring the total to 1.29 parts water. The mixture was stirred and 112 parts of methylene bis(cyclohexyl 4-isocyanate) were added. The NCO/OH ratio was 0.92. The mixture was heated to about 64° C., and 0.75 ml of stannous octoate was added. The mass was heated at 100° C. for about one hour.

The polymer formed a clear solution at 3% solids in a solution of 60/40 propylene glycol/water having a viscosity of 275 cps, and 2% solids in water having a viscosity of 122,000 cps, and at 2% solids in a solution of 20/80 propylene glycol/water having a viscosity of 13,200 cps. Solutions of the polymer at 0.2 to 3% in a diol/water and triol/water can be formulated for use in medical, cosmetic and industrial applications. Solutions of the polymer in a glycol/water solution can be injected into arthritic joints, so that body fluids displace the glycol and provide support for the joints.

The polymer formed a tough optically clear gel at 5% solids in a solution of 20/80 propylene glycol/water. The gel had good adhesion to the skin. The gel can be heated and flowed into a form used for electroconductive surgical pads and plastic surgery implants. An optically clear gel was formed at 10% solids in a solution of 20/80 propylene glycol/water for use in burn and wound care dressings and plastic surgery implants.

EXAMPLE 17

A mixture of 269 parts of 8000 polyoxyethylene diol, 114 parts of 1450 polyoxyethylene glycol and 12 parts of diethylene glycol was stirred and heated. The mixture was vacuum dried to a water content of 0.033 %, as measured by the Karl Fisher method, and 0.027 parts water was added to bring the total to 0.72 parts water. While continuing to stir, 59 parts of methylene bis(cyclohexyl- 4-isocyanate) were added, The NCO/OH ratio was 0.84. The mixture was heated to 66° C. and 1.0 ml of dibutyl tin dilaurate was added. The mass was heated at 100° C. for about one hour.

The polymer dissolved in 20/80 propylene glycol/water at 2.5% solids to form a solution having a viscosity of 100 cps, and at 5% solids having a viscosity of 14,500 cps. The polymer was mixed at 9% solids to form a gel in a 90/10 water/propylene glycol. The gel was heated and poured into a squeeze tube for use in burn and wound care dressings. The gel can be used for plastic surgery implants, electroconductive surgical pads, and industrial applications. Solutions of the polymer in diol/water and triol/water at 0.5 to 4% solids can be used for cosmetic, medical, and industrial applications.

EXAMPLE 18

A mixture of 393 parts of 8000 polyoxyethylene diol and 11 parts of diethylene glycol was stirred and heated. The mixture was vacuum dried to a water content of 0.0245%, as measured by the Karl Fisher method and 0.122 part water was added to bring the total to 0.22 part water. The mixture was stirred and 40 parts of methylene bis(cyclohexyl-4-isocyanate) were added. NCO/OH ratio was 0.92. The mixture was heated to 60° to 70° C., and 0.6 ml of stannous octate was added. The mass was heated at 100° C. for about one hour.

The polymer was insoluble in water at 2% solids, formed a very viscous gel at 2% solids in a solution of 20/80 propylene glycol, and formed an optically clear solution in a solution of 60/40 propylene glycol/water having a viscosity of 3640 cps. The polymer was mixed at 5% and 10% solids to form tough, soft and optically clear gels in a solution of 20/80 propylene glycol/water. The gels can be used in burn and wound care dressings, plastic surgery implants, heat and cold retentive and pressure absorbing products such as packs for backaches and arthritic pains, industrial, and cosmetic applications such as face and body creams and deodorants. A 30-gram weight moved 1.6 centimeters in 30 minutes, 0.053 cm/min, through 150 grams of the 5% gel in an 8-ounce Jar.

EXAMPLE 19

A mixture of 402 parts of 8000 polyoxyethylene diol having 11.2 parts of diethylene glycol was agitated and heated. The heated mixture was vacuum dried and additional water was added to bring the total water to 0.14 parts. The mixture was stirred and 42.2 parts of methylene bis(cyclohexyl-4-isocyanate) were added. The NCO/OH ratio was 0.975. The mixture was heated to 60° C to 65° C. and 0.38 ml of dibutyl tin dilaurate was added. The polymer mass was heated at 100° C. for about one hour.

The polymer was dissolved at 3% solids in a solution of 60/40 propylene glycol/water to provide a viscosity of 73 cps, and at 2% solids in 20/80 propylene glycol/water with a viscosity of 395 cps, and at 2% in water with a viscosity of 2280 cps. The polymer formed tough gels at 15%, 17% and 19% solids in a solution of 20/80 propylene glycol/water. The respective amount of polymer was added as 85%, 83%, and 81% of the solution of 20/80 propylene glycol/water and mixed on the roller mill for an hour, then heated in an oven for about 1–2 hours at 80°–90° C. The mixture was placed on the roller mill until a uniform gel was obtained. The gel was heated and poured into a flat mold and placed in water. The 15%, 17% and 19% concentration gels absorbed water to the extent of respectively 1.3, 1.4, and 1.5 grams per gram of gel. The gels can be used in burn and wound care applications, plastic surgery implants, drug delivery systems, and electroconductive surgical pads.

EXAMPLE 20

Gels and solutions made in Examples 1, 6, 15, 16, and 18 were tested for viscosity and integrity. A 30-gram stainless steel weight was allowed to move through 150 grams of gel in an 8-ounce jar. The distance the ball moved in 30 minutes or less was noted. The following results are set forth below:

TABLE 1

| Test | Ex No. | Polymer % | Media | Distance Cm | cm/min |
|---|---|---|---|---|---|
| 1 | 1 | 5 | 2/8 PG/water | 7.5 | .25 |
| 2 | 6 | 15 | 2/8 PG/water | 0.8 | .027 |
| 3 | 15 | 10 | 2/8 DEG/water | 6.5 | 7.8 |
| 4 |  | 10 | 2/8 IPA/water | 2.5 | .08 |
| 5 |  | 10 | 2/8 Eth/water | 6.5 | 39 |
| 6 |  | 10 | 2/8 DPG/water | 7 | .23 |
| 7 | 16 | 5 | 2/8 PG/water | 6 | .20 |
| 8 |  | 7 | 2/8 PG/water | 3.5 | .116 |
| 9 |  | 10 | 2/8 PG/water | 1 | .033 |
| 10 | 18 | 10 | 2/8 PG/water | 1 | .033 |

Wherein PG is propylene glycol; DEG is diethylene glycol; Eth is ethanol; IPA is isopropyl alcohol; DPG is dipropylene glycol.

For test 5 the ball reached the bottom of the jar in 50 seconds. For test 4, the ball reached the bottom of the jar in 10 seconds.

EXAMPLE 21

A mixture of 400 parts of polyethylene glycol having an average molecular weight of 8000, 11 parts of diethylene glycol and 1.18 parts of diglycolamine were mixed and heated to 65° C. Vacuum was applied to the heated mixture until about 0.054% of moisture was obtained, and 0.007 gram of water was added to the mixture. While continuing the stirring, 41.8 parts of methylene bis(cyclohexyl-4-isocyanate) was added during which the temperature decreased. When the temperature reached about 70° C., 0.37 ml of dibutyl tin dilaurate was added, and the mass exothermed to 75° C. The mass was then poured into a polypropylene pan and held at 100° C. for about one hour to complete formation of the polymer.

The polymer was dissolved at 3% solids in a 60/40 propylene glycol/water to provide a viscosity of 57 cps. The polymer formed a tough, resilient and clear gel at 19% solids in 20/80 propylene glycol/water which impeded a 30-gram steel ball at about 180 grams in a jar, to about 8 mm over 30 minutes at room temperature and about 16 mm over 10 minutes at 37° C. The polymer has a viscosity of 48 cps at 2% solids in a 20/80 propylene glycol/water solution. The polymer had very good slip properties when used as a coating over a plastic surface.

EXAMPLE 22

A mixture of 402 parts of polyethylene glycol having an average molecular weight of 8000, 11 parts of diethylene glycol and 0.93 parts of LG650, a triol made by ARCO, were mixed and heated to 65° C. Vacuum was applied to the heated mixture until about 0.034% of moisture was obtained, and 0.087 gram of water was added to the mixture. While continuing the stirring, 40.6 parts of methylene bis-(cyclohexyl-4-isocyanate) was added during which the temperature decreased. When the temperature reached about 58° C., 0.37 ml of dibutyl tin dilaurate was added, and the mass exothermed to 60° C. The mass was then poured into a polypropylene pan and held at 100° C. 5 for about one hour to complete formation of the polymer.

The polymer was dissolved at 3% solids in 60/40 propylene glycol/water solution to provide a viscosity of 98 cps. The polymer formed a tough gel at 19% solids in 20/80 propylene glycol/water solution which impeded a 30-gram steel ball at about 180 grams in a jar, to a rate of 0.1 mm/min and to a rate of 1.3 mm/min at 37° C. The polymer had a viscosity of 510 cps at 2% solids in 20/80 propylene glycol/water solution.

EXAMPLE 23

A mixture of 377 parts of polyethylene glycol having an average molecular weight of 8000, 11 parts of diethylene glycol and 22.6 parts of polyethylene glycol having an average molecular weight of 1450 were mixed and heated to 65° C. Vacuum was applied to the heated mixture until about 0.051% of moisture was obtained, and 0.181 gram of water was added to the mixture. While continuing the stirring, 44.2 parts of methylene bis(cyclohexyl-4-isocyanate) were added during which the temperature decreased. When the temperature reached about 58° C., 0.37 ml of dibutyl tin dilaurate was added and the mass exothermed to 61° C. The mass was then poured into a polypropylene pan and held at 100° C. for about one hour to complete formation of the polymer.

The polymer was dissolved at 3% solids in 60/40 propylene glycol/water to provide a viscosity of 86 cps. The polymer formed a tough clear gel at 19% solids in 20/80 propylene glycol/water which impeded a 30-gram steel ball at about 180 grams in a jar, to a rate of 0.27 mm/min and to a rate 2.3 mm/min at 37° C. The polymer had a viscosity of 180 cps at 2% solids in 20/80 propylene glycol/water.

EXAMPLE 24

A mixture of 14026 parts of 8000 polyoxyethylene diol and 392 parts of diethylene glycol was agitated and heated in a reactor. The mixture was vacuum dried at about 180° F. to 0.055% water and 10.4 parts water were added to bring the total in the reaction mixture to 18.3 parts. A separate reactor contained 1454 parts of methylene bis(cyclohexyl-4-isocyanate). To the diols was added 23.8 cc of dibutyl tin dilaurate. Then the solids and catalyst were heated at 175to 185° F. and the isocyanate was heated to 110–115° F. and both liquids were forced out at under nitrogen pressure using a piston cylinder at about a ratio of 0.101. Twelve shots of liquid were pumped into a polypropylene tub and heated for one hour at 100° C. The NCO/OH ratio was 0.84.

The polymer was dissolved at 3% solids in a solution of 60/40 propylene glycol/water to provide a viscosity of 57 cps and at 2% solids in a solution of 20/80 propylene glycol/water to provide a viscosity of 63 cps. The polymer can be dissolved at 15% solids in a 10/90 propylene glycol/water solution, heated to about 80° C., and cooled to about 45° C., a drug can be added, and cooled to room temperature. The gel can be used to deliver a drug through the skin. The polymer was mixed with a solution of 20/80 propylene glycol/water at polymer concentrations of 17%, 19% and 21% and heated to about 80° C. to form gels and poured into wound care forms. The gels had respective absorbencies of greater than 2.75, 4.14 and 3.02 grams per gram of gel. The gels can be used for burn and wound care dressings and plastic surgery implants. The gels were tough at room and at body temperature.

EXAMPLE 25

A mixture of 322 parts of polyoxyethylene diol having an average molecular weight of 8000, 11.2 parts of diethylene glycol, 47 part of ethylhexyl diol, and 70 parts of polyethylene glycol having an average molecular weight of 1450 were mixed and heated to 65° C. Vacuum was applied to the heated mixture until about 0.05% of moisture was obtained, and 0.255 gram of water was added to the mixture to provide a total of 0.46 part. While continuing the stirring, 48 parts of methylene bis(cyclohexyl-4-isocyanate) were added during which the temperature decreased. When the temperature reached about 60° C., 1 ml of dibutyl tin dilaurate was added, and the mass exothermed to 67° C. The mass was then poured into a polypropylene pan and held at 100° C. for about one hour to complete formation of the polymer.

The polymer formed uniform gels at 2% in 40/60 propylene glycol/water and at 4% in 60/40 propylene glycol/water. The polymer was insoluble in water and had a water content of 87% and a linear expansion of 102% after 24 hours in water.

EXAMPLE 26

A mixture of 322 parts of polyoxyethylene diol having an average molecular weight of 8000, 11.2 parts of diethylene glycol, 0.90 part of LG-650, a triol made by ARCO, and 70 parts of polyethylene glycol having an average molecular weight of 1450 were mixed and heated to 65° C. Vacuum was applied to the heated mixture until about 0.02% of moisture was obtained, and 0.039 gram of water was added to the mixture to provide a total of 0.044 gram. While continuing the stirring, 52 parts of methylene bis(cyclohexyl-4-isocyanate) were added during which the temperature decreased. When the temperature reached about 67° C., 0.69 ml of stannous octoate was added, and the mass exothermed to 80° C. The mass was then poured into a polypropylene pan and held at 100° C. for about one hour to complete formation of the polymer.

The polymer formed uniform gels at 2% in 40/60 propylene glycol/water.

EXAMPLE 27

A mixture of 402 parts of polyoxyethylene diol having an average molecular weight of 8000, 11.2 parts of diethylene glycol, and 0.93 part of ethylhexyl diol were mixed and heated to 65° C. Vacuum was applied to the heated mixture until about 0.05% of moisture was obtained, and 0.26 gram of water was added to the mixture to provide a total of 0.46 part. While continuing the stirring, 49 parts of methylene bis(cyclohexyl-4-isocyanate) were added during which the temperature decreased. When the temperature reached about 60° C., 1 ml of dibutyl tin dilaurate was added, and the mass exothermed to 68° C. The mass was then poured into a polypropylene pan and held at 100° C. for about one hour to complete formation of the polymer.

The polymer formed uniform gels at 2% in 40/60 propylene glycol/water and had a viscosity of two million centipoises at 3% in 60/40 propylene glycol/water.

EXAMPLE 28

A mixture of 402 parts of polyoxyethylene diol having an average molecular weight of 8000, and 11.2 parts of diethylene glycol were mixed and heated. Vacuum was applied to the heated mixture until about 0.05% of moisture was obtained, and 0.26 gram of water was added to the mixture to provide a total of 0.46 part. While continuing the stirring, 47 parts of methylene bis(cyclohexyl-4-isocyanate) were added during which the temperature decreased. When the temperature reached about 60° C., 1 ml of dibutyl tin dilaurate was added, and the mass exothermed to 68° C. The mass was then poured into a polypropylene pan and held at 100° C. for about one hour to complete formation of the polymer.

The polymer formed a soft elastic gel at 10% in 40/60 propylene glycol/water and pressed film of the polymer had a water content of 87% and a linear expansion of 104% after 24 hours immersion in water. The polymer coating had very good slip after 7, 14 and 21 days, namely values of 0.039, 0.035, and 0.032 coefficient of friction.

EXAMPLE 29

A mixture of 234 parts of polyoxyethylene diol having an average molecular weight of 8000, 99 parts of polyoxyethylene diol having an average molecular weight of 1450, 46 parts of polyetherpolycarbonate having an average molecular weight of 2000, 10 parts of diethylene glycol, and 0.92 part of ethylhexyl diol were mixed and heated to 65° C. Vacuum was applied to the heated mixture until about 0.04% of moisture was obtained, and 0.54 gram of water was added to the mixture to provide a total of 0.69 parts. While continuing the stirring, 64 parts of methylene bis(cyclohexyl-4-isocyanate) were added during which the temperature decreased. When the temperature reached about 50° C., 0.68 ml of dibutyl tin dilaurate was added, and the mass exothermed to 70° C. The mass was then poured into a polypropylene pan and held at 100° C. for about one hour to complete formation of the polymer.

The polymer formed a uniform solution at 2% in 40/60 propylene glycol/water with a viscosity of 920 cps, and formed a soft uniform gel with excellent payoff at 5% in 40/60 propylene glycol/water.

EXAMPLE 30

A mixture of 232 parts of polyoxyethylene diol having an average molecular weight of 8000, 98 parts of polyoxyethylene diol having an average molecular weight of 1450, 21 parts of polyetherpolycarbonate having an average molecular weight of 2000, 10 parts of diethylene glycol, and 0.91 part of ethylhexyl diol were mixed and heated to 65° C. Vacuum was applied to the heated mixture until about 0.03% of moisture was obtained, and 0.54 gram of water was added to the mixture to provide a total of 0.66 parts. While continuing the stirring, 60 parts of methylene bis(cyclohexyl-4-isocyanate) were added during which the temperature decreased. When the temperature reached about 50° C., 0.68 ml of dibutyl tin dilaurate was added, and the mass exothermed to 70° C. The mass was then poured into a polypropylene pan and held at 100° C. for about one hour to complete formation of the polymer.

The polymer formed a uniform solution at 2% in 40/60 propylene glycol/water with a viscosity of 3300 cps, and formed a soft uniform gel with excellent payoff at 10% in 40/60 propylene glycol/water.

EXAMPLE 31

A mixture of 266 parts of polyoxyethylene diol having an average molecular weight of 8000, 11 parts of diethylene glycol, 112 parts of polyoxyethylene diol having an average molecular weight of 1450, 10 parts of 1,3-ethylhexyl diol were mixed and heated to 65° C. Vacuum was applied to the heated mixture until about 0.03% of moisture was obtained, and 0.61 gram of water was added to the mixture to provide a total of 0.72 parts. While continuing the stirring, 80 parts of methylene bis(cyclohexyl-4-isocyanate) were added during which the temperature decreased. When the temperature reached about 62° C., 0.72 ml of dibutyl tin dilaurate was added, and the mass exothermed to 75° C. The mass was then poured into a polypropylene pan and held at 100° C. for about one hour to complete formation of the polymer.

The polymer had a viscosity of 240 cps in 40/60 propylene glycol/water, and a pressed sample had a very good slip, was soft, and strong. The pressed film had a water content of 92% and a linear expansion of 143% after immersion in water. The polymer may be used as a high slip coating for catheters, metals for use in blades and razors, and for high slip biocompatible materials.

EXAMPLE 32

A mixture of 393 parts of polyoxyethylene diol having an average molecular weight of 8000, 11 parts of diethylene glycol, were mixed and heated to 65° C. Vacuum was applied to the heated mixture until about 0.02% of moisture was obtained, and 0.12 gram of water was added to the mixture to provide a total of 0.22 part. While continuing the stirring, 40 parts of methylene bis(cyclohexyl-4-isocyanate) were added during which the temperature decreased. When the temperature reached about 60° C., 0.6 ml of dibutyl tin dilaurate was added, and the mass exothermed to 75° C. The mass was then poured into a polypropylene pan and held at 100° C. for about one hour to complete formation of the polymer.

EXAMPLE 33

A mixture of 402 parts of polyoxyethylene diol having an average molecular weight of 8000, 11 parts of diethylene glycol, and 14 parts of AR11-34 made by ARCO were mixed and heated to 65° C. Vacuum was applied to the heated mixture until about 0.05% of moisture was obtained, and 0.27 gram of water was added to the mixture to provide a total of 0.47 parts. While continuing the stirring, 48 parts of methylene bis(cyclohexyl-4-isocyanate) were added during which the temperature decreased. When the temperature reached about 60° C., 1 ml of dibutyl tin dilaurate was added, and the mass exothermed to 68° C. The mass was then poured into a polypropylene pan and held at 100° C. for about one hour to complete formation of the polymer.

2% of the polymer was insoluble in 20/80 propylene glycol/water, had a viscosity of 3640 cps in 60/40 propylene glycol/water, and was pressed into a film that had a water content of 94% and a linear expansion of 186%. The polymer can be used in high slip products such as coatings and catheters.

EXAMPLE

A mixture of 266 parts of polyoxyethylene diol having an average molecular weight of 8000, 112 parts of polyoxyethylene diol having an average molecular weight of 1450, 11 parts of diethylene glycol, 0.45 part of ethylhexyldiol, and 0.91 part of cyclohexanediol were mixed and heated. Vacuum was applied to the heated mixture until about 0.08% of moisture was obtained, and 0.36 gram of water was added to the mixture to provide a total of 0.68 part. While continuing the stirring, 65 parts of methylene bis(cyclohexyl-4-isocyanate) were added during which the temperature decreased. When the temperature reached about 60° C., 0.68 ml of dibutyl tin dilaurate was added, and the mass exothermed to 80° C. The mass was then poured into a polypropylene pan and held at 100° C. for about one hour to complete formation of the polymer.

At a concentration of 2%, the polymer had a viscosity of 2650 cps in 40/60 propylene glycol/water, and at 5%, the polymer formed a soft sticky gel.

While the invention has been described with reference to the preferred embodiment, this description is not intended to be limiting. It will be appreciated by those of ordinary skill in the art that modifications may be made without departing from the spirit and scope of the invention.

We claim:

1. A hydrophilic polyether polyurethane polymer of improved absorption and slip properties comprising the reaction product of a mixture of:

a long chain polyoxyalkylene glycol, said polyoxyalkylene glycol selected from the group consisting of polyoxyethylene glycol having a number average molecular weight of about 400 to about 20,000, and polyoxypropylene glycol having a number average molecular weight of about 200 to about 4,000, the amount by weight of said polyoxyalkylene glycol in the reaction mixture being from about 20% to about 96%;

a glycol selected from the group consisting of ethylene glycol, propylene glycol, 2-ethyl-1,3-hexanediol, tripropylene glycol, triethylene glycol, 2,-4-pentanediol, 2-methyl-1,3-propanediol, cyclohexanediol, cyclohexanedimethanol, 2-methyl-1,3-pentanediol, dipropylene glycol, diethylene glycol and mixtures thereof having a number average molecular weight of about 1,000 to about 9,000;

an organic diisocyanate; and a urea equivalent, said urea equivalent is formed from an amount of about 0.02% to about 0.4% of water in the reaction mixture, the ratio of NCO to OH of the long chain polyoxyalkylene glycol, the alkylene glycol and the water being from about 0.84 to about 0.97;

wherein a solution of the reaction product at a 3% concentration in a propylene glycol to water solution has a viscosity in the range of about 1 to about 2,000,000 cps.

2. The polymer of claim 1 wherein said urea equivalent is formed from an amount of about 0.01% to about 0.08% water and about 0.03% to about 10.0% amine, said amine being selected from the group consisting of ethylene diamine, propylene diamine, monoethanol amine and diglycol amine.

3. The polymer of claim 2 wherein said amine is diglycol amine.

4. The polymer of claim 1 3further comprising an amount of about 0.01% to about 5.0% of a triol.

5. The polymer of claim 4 wherein the amount of said triol in the reaction mixture is from about 0.03% to about 0.2%.

6. The polymer of claim 1 wherein the amount by weight of said polyoxyalkylene in the reaction mixture is at least about 55% of the reaction components.

7. The polymer of claim 1 wherein the viscosity is in the range of about 4 cps to about 500,000 cps in a 20/80 propylene glycol to water solution.

8. A high slip material formed of the polymer of claim 1.

9. The polymer of claim 1 wherein the amount by weight of said polyoxyalkylene glycol is at least about 50% of the reaction components, about 0.001% to about 5.0% of a triol, and wherein the urea equivalent comprises an amount of water of about 0.005% to about 0.3% the polymer further comprising a hydrophobic diol of about 0.01% to about 3.0%.

10. A high slip coating formed of the polymer of claim 9.

11. A hydrophilic polyether polyurethane polymer of improved strength and integrity comprising the reaction product of a diol comprising a high molecular weight long chain polyoxyalkylene glycol, said polyoxyalkylene glycol selected from polyoxyethylene glycol having a number average molecular weight of 4,000 to 12,000, mixed with a low molecular weight polyoxyethylene having a number average number molecular weight of about 400 to about 2,000;

a low molecular weight alkylene glycol selected from ethylene glycol, propylene glycol, dipropylene glycol, and diethylene glycol and mixtures thereof the amount by weight of said high molecular weight polyoxyethylene in the reaction mixture being from at least about 30%;

an organic diisocyanate; and water in an amount by weight of about 0.01% to about 0.4% of the reaction mixture for the high molecular weight polyoxyethylene and about 0.01% to about 0.35% for the mixture of the high molecular weight and the low molecular weight polyoxyethylene glycol, the ratio of NCO to OH of the high molecular weight and low molecular weight polyoxyalkylene glycol, the alkylene glycol and the water from being about 0.70 to about 0.99.

wherein the reaction product of a 3% concentration in a 40/60 glycol to water solution has a viscosity in the range of 1 to 500,000 cps.

* * * * *